United States Patent [19]

Matsuoka et al.

[11] Patent Number: 4,861,453
[45] Date of Patent: Aug. 29, 1989

[54] CORROSION DETECTING PROBE FOR STEEL BURIED IN CONCRETE

[75] Inventors: Kazumi Matsuoka; Hiroshi Kihira; Satoshi Ito; Tomomi Murata, all of Kawasaki, Japan

[73] Assignee: Nippon Steel Corporation, Tokyo, Japan

[21] Appl. No.: 137,027

[22] Filed: Dec. 23, 1987

[30] Foreign Application Priority Data

Dec. 26, 1986 [JP] Japan .................................. 61-310706

[51] Int. Cl.⁴ ............................................. G01N 27/46
[52] U.S. Cl. .................................... 204/404; 204/412; 204/435
[58] Field of Search ................. 204/1 C, 404, 412, 435

[56] References Cited

U.S. PATENT DOCUMENTS 4,695,360  9/1987  Asatiani et al. ..................... 204/404

FOREIGN PATENT DOCUMENTS 6129457  8/1979  Japan .
61-33380  6/1980  Japan .
59-237146  12/1984  Japan .

OTHER PUBLICATIONS

Corrosion 987, Mar. 9-13, 1987, "Monitoring of Corrosion of Reinforcing Bar in Concrete", K. Matsuoka, Paper Number 121.

*Primary Examiner*—T. Tung

[57] ABSTRACT

A corrosion detecting probe is to be used in combination with a known electrochemical measuring apparatus for inspecting corrosion state of a steel material buried in a concrete structure. The probe comprises a container made of an electrically insulating material and having an open end adapted to be placed in close contact with a surface of the concrete structure, a cover closing the open end and made of a porous and liquid permeable material, an electrolyte liquid solution filling the container so that the cover is sufficiently impregnated with the solution, and an electrode assembly mounted within the container so as to be immersed at least partially in the electrolyte solution. The electrode assembly includes an elongated reference electrode having a free end portion at least partially immersed in the electrolyte solution, a counter electrode having an electrode plate of a symmetrical configuration with respect to the free end portion of the reference electrode and distanced therefrom, and a current flow line control electrode having an electrode plate of a symmetrical configuration with respect to the free end portion of the reference electrode and disposed in a same plane as the electrode plate of the counter electrode at a distance therefrom.

6 Claims, 8 Drawing Sheets

F I G. 9
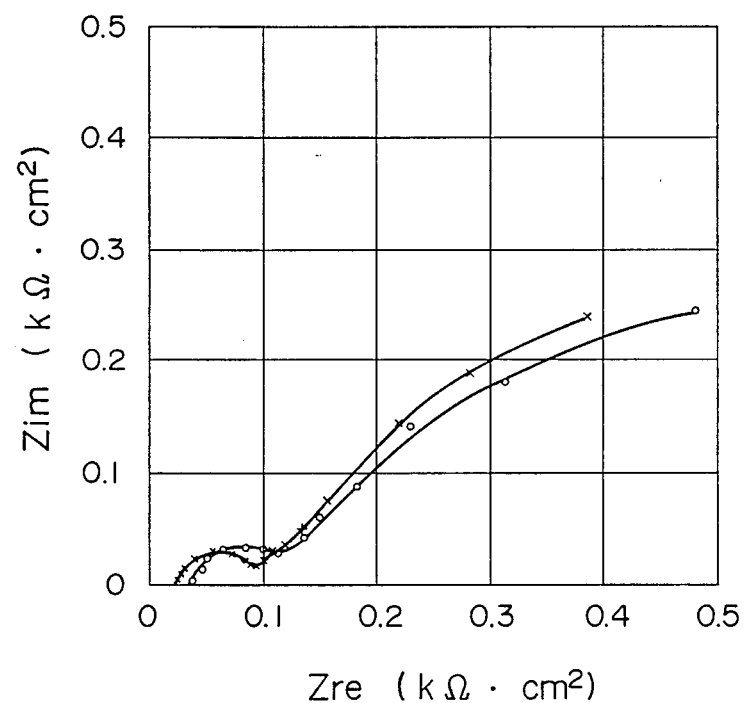

CORROSION DETECTING PROBE FOR STEEL BURIED IN CONCRETE

BACKGROUND OF THE INVENTION

1. Field of the Invention

The present invention relates generally to a corrosion detecting probe for detecting corrosion of steel materials buried in existing armored concrete structures and more particularly concerns a transportable corrosion detecting probe which is capable of quantitatively determining the state of corrosion through an electrochemical measurement.

2. Description of the Related Art

The steel materials employed in the armored or reinforced concrete structures such as buildings are subjected to corrosion under various conditions and undergo degradation in the function. Under the circumstances, it is a common practice at present to examine or measure the degree of corrosion of the steel material and determine the use life of the reinforced concrete structure on the basis of the result of the measurement. To this end, there is generally adopted a method of inspecting the steel material according to which a concerned structure of armored concrete is partially destroyed to expose a reinforcing steel member for performing visual inspection thereof. However, this type of inspection is obviously unfavorable for the structure or building itself.

As an attempt to evade the problem mentioned above, there has been proposed a method of determining or measuring nondestructively the corrosion of steel material in the state buried or embedded in the concrete structure, as is exemplified by the one disclosed in Japanese Patent Application Laid Open No. JP-A-59-217147. According to this prior art method, a steel bar embedded in a concrete structure is partially exposed to be used as a working electrode to which a test electrode terminal is connected. On the other hand, a transportable electrode device including a combination of a reference electrode and a counter electrode both immersed in a liquid electrolyte solution is moved sequentially over the concrete surface in intimate or close contact therewith along a path where the steel bar to be inspected is embedded, wherein the rest potential, polarization resistance and solution resistance are measured with the aid of the abovementioned reference electrode, working electrode and the counter electrode. On the basis of these three electrochemical characteristic quantities as measured, the state or level of corrosion of the steel material is estimated.

In this connection, a method of measuring effectively the corrosion susceptibility of a local portion of an elongated metal member in an electrolyte solution without need for coating the member with an insulation material except for the local portion of concern is disclosed in Japanese Patent Publication No. 61-29457. Additionally, an application of this method to a multipoint measurement is disclosed in Japanese Patent Publication No. 61-33380.

The prior known corrosion detecting techniques mentioned above however suffer from difficulties described below when they are to be used for the nondestructive measurement of the steel material embedded in the concrete structure.

In the first place, description will be made of the corrosion measuring method proposed in JP-A-59-217147 by reference to FIGS. 2 and 3 of the accompanying drawings. According to this method, a steel bar 8 embedded in a concrete structure is used as a working electrode and attached with a working electrode terminal 9 at a portion exposed only partially, while a transportable electrode device 1 including a combination of a reference electrode 4 and a counter electrode 5 both immersed in a liquid electrolyte solution 3 is placed on the surface of the concrete structure in close contact therewith sequentially over a number of locations along the embedded length of the steel bar 8, wherein at each of the above-mentioned locations, the rest potential, polarization resistance and the solution resistance are measured by means of the reference electrode 4, the working electrode 9 and the counter electrode 5. On the basis of the three electrochemical characteristic values thus obtained, the state or level of corrosion is estimated. This method is certainly advantageous in that the steel member embedded in concrete can be measured nondestructively. FIG. 2 shows graphically distributions of current flow lines 31 and equipotential lines 32 which make appearance when a certain voltage is externally applied between the counter electrode 5 and the working electrode 9, which certain voltage is determined with reference to the rest potential (i.e. the potential making appearance across the reference electrode 4 and the working electrode 9 in the state where no external potential is applied between the counter electrode 4 and the working electrode 9. As will be seen in FIG. 2, the current flowing to the steel member 8 embedded in the concrete structure from the counter electrode 5 disposed within the transportable electrode device 1 propagates extensively, while the range within which the current flow takes place differs remarkably in dependence on the thickness h of the concrete layer 7, giving rise to problems. For determining the influence brought about by the factors mentioned above, simulation is performed on an electrically conductive paper sheet of a size comparable to that of an actual concrete surface to be tested. The results of the simulation are graphically illustrated in FIG. 3, in which the ratio of current density $i/i_0$ in the steel member embedded in concrete (where $i_0$ represents the current density (in $A/cm^2$) measured in the steel portion located immediately underneath the transportable electrode device 1) is taken along the ordinate with the abscissa representing the distance L, from the point underlying immediately below the transportable electrode device. Comparison of the two curves shows clearly that the current distribution represented by the curve marked with a series of x for the case where h=30 mm differs remarkably from the current distribution represented by the curve attached with small circles for the case where h=50 mm. Needless to say, the electrochemical characteristic quantities such as the polarization resistance $R_p$ ($\Omega\ cm^2$) and the solution resistance $R_s$ ($\Omega\ cm^2$) are only meaningful when they can be defined on the basis of the current flow per unit area. It will however be noted that in the case of the method described above, the surface region of the steel bar 8 which exerts influence to the measurement can not be limited only to a small area to be measured. As a consequence, the polarization resistance and the solution resistance measured at various locations on the concrete surface are influenced by the thickness h of the concrete coating, thus making it meaningless to compare simply the measured resistance values.

Next, reference is made to the methods disclosed in Japanese Patent Publications Nos. 61-29457 and 61-33380. Both of these methods teach that when a local portion of an elongated metal member is to be measured in respect to the corrosion susceptibility within a liquid electrolyte solution, measurement can be performed with high efficiency without coating the metal member except for the local portion to be subjected to the direct measurement. More specifically, these known methods are advantageous in that the electrochemical measurement can be accomplished on the basis of the current measured only at the local surface region of the steel member of concern by virtue of such electrode structure that a probe electrode (hereinafter referred to as the counter electrode) is enclosed by a guard electrode (hereinafter referred to as the current flow line control electrode). However, these prior art methods are incapable of conducting the corrosion measurement nondestructively for the steel member embedded in the concrete structure for the reasons elucidated below. First, the method disclosed in Japanese Patent Publication No. 61-29457 suffers from two problems:

(1) It is impossible to ensure electrically preferable conduction in a nondestructive manner between a steel material of concern embedded in a concrete structure and the concerned electrode of the detecting probe.

(2) Any accurate measurement of potential is rendered impractical with the reference electrode disposed in the vicinity of the corrosion detecting probe which is composed of a counter electrode and a current flow line control electrode.

Since the problem (1) is self-explanatory, any further discussion will be unnecessary. Accordingly, following discussion is directed to the problem (2).

Assuming that the problem (1) is solved by some suitable measures and that the method disclosed in Japanese Patent Publication No. 61-29457 is to be applied for evaluation of the corrosion of a steel member buried in a concrete structure, then disposition of the individual electrodes upon actual measurement will be such as shown in FIG. 4 of the accompanying drawings. More specifically, the corrosion detecting probe 13 composed of the counter electrode 5 and the current flow line control electrode 11 is disposed at a position 16a above the steel member 8 with a distance of 20 mm to 50 mm, as is in the case of the conventional measurement.

In that case, the problem to be first pointed out is seen in that the rest potential of the steel member in the corroded state which usually differs in dependence on the position of measurement can not be measured at the point 16b on the concrete surface located nearest to the surface point 16a of the steel member of concern, but the potential of a value approximating that of the rest potential appearing at the point 16c on the surface of the steel member of concern will be measured, because the position of the surface point 16a of the steel member 8 which is really the subject for measurement is deviated from the location 16d where the reference electrode 4 is disposed.

Even when the first problem mentioned above is solved by realizing the corrosion detecting probe 13 in as small a size as possible or by any other appropriate means, to thereby minimize error involved in the measurement of the rest potential, there still arises another problem in conjunction with the electrochemical measurement (e.g. measurement of polarization or AC impedance) carried out by applying a certain voltage determined with reference to the rest potential of the steel member 8 between the latter and the counter electrode 5, which is electrically connected to the current flow line control electrode 11, to thereby produce current flows thereacross.

First, the problem intervening the polarization measurement will be considered. As will be seen from a potential/current distribution map depicted in FIG. 4 on the basis of the results of analysis of the actual measurement, equipotential lines are much concentrated below the current flow line control electrode 11. As a consequence, the potential difference measured between the steel member 8 and the reference electrode 4 which is located in the vicinity of the current flow line control electrode 11 will vary significantly even when the point 16d where the reference electrode 4 is positioned is deviated only slightly. Magnitude of such change in the measured potential will become more significant as the voltage applied across the steel member 8 and the electrodes 5, 11 is increased. This holds true even in case the reference electrode 4 can be stationally secured with a high accuracy at a predetermined distance relative to the corrosion detecting probe 13 by some suitable means, because the thickness h of the concrete layer is not usually uniform in strict sense but varies more or less in dependence on the position at which the corrosion detecting probe 13 is disposed, whereby the location within the body of concrete to which the measured potential value bears relevancy (the location 16e in the case of the illustrated example) can not be determined definitely. As the result, for the polarization measurement in which correction or compensation is required for ohmic voltage drop (IR loss of potential), extremely complicate procedure is involved because correction must be made on the ohmic voltage measured between the locations 16a and 16e upon every measurement after the potential and current distributions have been analyzed in detail for identifying accurately the location (16e) where the potential is detected. This problem becomes more serious in the measurement in which a system of high resistance such as concrete intervenes.

Next, the problem associated with the measurement of AC impedance will be considered. In the case of the AC impedance measurement, influence of the ohmic drop of potential does not present any noticeable problem, but there arises instead a problem that the current distribution varies remarkably in dependence on the frequency employed in the AC impedance measurement, which will be elucidated below. FIG. 5 of the accompanying drawings illustrates an experimental simulation of the AC impedance measurement performed by using an electrically conductive paper sheet. In the figure, a reference numeral 18 denotes generally an electrode unit composed of two electrodes of the corrosion detecting probe, 17 denotes a concrete structure, 19 denote a plurality of divided steel surface segments, 20 and 21 denote capacitors and resistors each connected in parallel for representing a corrosion equivalent circuit, 14 denotes a non-resistance type ampere meter, and a reference numeral 23 denotes an AC power supply source. In this experiment, values of the currents flowing through the steel segments 19 were measured by using AC currents of two different frequencies f (e.g. f=10 Hz and 1 KHz). The results obtained in the measurement are graphically illustrated in FIG. 6, in which logarithmic value of the current i (mA) per segment is taken along the ordinate with the segment identification number being taken along the abscissa. As will be seen in FIG. 6, the currents flowing through the individual segments vary as a function of the frequency, which in turn means that the voltage and current distributions illustrated in FIG. 4 also undergo variation as a function of the frequency employed in the measurement. More specifically, since the essential feature of the corrosion measurement by the AC impedance method resides in that the current flow between the steel member 8 buried in concrete and the two electrodes (i.e. the counter electrode 5 and the current flow line control electrode 11) incorporated in the corrosion detecting probe is controlled with reference to the potential at the location 16d (same potential as that at the location 16e) where the reference electrode is positioned, the actual voltage applied across the steel member and the electrodes not only can be established definitely but also undergoes variation in dependence on the frequency employed in the measurement. As the result, the impedance value determined arithmetically by using a conventional electrochemical measuring/analysis apparatus 15 is necessarily poor in accuracy.

Finally, the problem which will occur when the method disclosed in Japanese Patent Publication No. 33380/1986 is applied to evaluation of corrosion of the steel material embedded in the concrete structure will be touched briefly. This known method shares the basic concept with the one disclosed in Japanese Patent Publication No. 61-29457 and allows a multi-point measurement to be performed with a plurality of counter electrodes disposed as the current control electrodes. Accordingly, the method under consideration naturally suffers from the same problem as that of the method disclosed in the last mentioned publication. Besides another problem arises additionally. Because the multi-point measurement is performed by using the reference electrode disposed at a given position, the result of the multi-point measurement will be of no use for evaluation of corrosion for such species of object in which the rest potential exhibiting different values in dependence on the location is of great importance for evaluation of the corrosion (such as, for example, for the evaluation of corrosion of the steel member in the longitudinal direction).

As will now be understood from the foregoing discussion, the aforementioned problem (2) provides a great obstacle in the electrochemical measurement of steel member embedded in a concrete structure as compared with the measurement within the electrolyte solution where the position of the reference electrode can be selected arbitrarily.

SUMMARY OF THE INVENTION

An object of the present invention is to provide a corrosion detecting probe for measuring electrochemical characteristic quantities for use in evaluation of corrosion state of a steel member embedded or buried in a concrete structure which probe is destined to be employed in cooperation with a known electrochemical measurement apparatus including a power supply source for generating a controlled voltage and a working electrode terminal for coupling one end of the power supply source to the steel member. The probe includes a counter electrode connected to the other end of the power supply source and a reference electrode and is adapted to be brought into close contact with a surface location of the concrete structure corresponding to a local region of the steel member to be measured for obtaining predetermined electrochemical characteristic quantities by applying the controlled voltage from the power supply source to the steel member by way of the working electrode terminal and to the counter electrode. The probe is so arranged that the measurement value is sensitive only to the influence originating in the corrosion state of a steel surface location of concern but substantially insensitive to the corrosion state of the steel member in other regions thereof.

In view of the above object, there is provided according to one embodiment of the present invention a corrosion detecting probe which comprises a container including an open end brought into close contact with the surface of a concrete layer coating a steel material constituting the object to be measured and a cover fitted in the open end and made of a water permeable material, the container being filled a liquid electrolyte solution to such a level that the water permeable material is adequately impregnated with the electrolyte solution, and an electrode assembly including an elongated reference electrode immersed in the electrolyte solution at least at a free end portion thereof, a counter electrode having an electrode plate disposed around the free end portion of the reference electrode at a distance therefrom and immersed in the electrolyte solution. The electrode plate of the counter electrode is preferably composed of a pair of symmetrical segments arrayed in a symmetrical relation with respect to the free end portion of the reference electrode, and a current flow line control electrode disposed outside of the counter electrode and having an electrode plate immersed in the electrolyte solution. The electrode plate of the current flow line control electrode is preferably composed of a pair of symmetrical segments which are symmetrical with reference to at least the free end portion of the reference electrode and aligned with the pair of symmetrical segments of the electrode plate of the counter electrode.

BRIEF DESCRIPTION OF THE DRAWINGS

FIG. 9 is a view for graphically illustrating the results of AC impedance measurement carried out with the corrosion detecting probe according to the invention;

DESCRIPTION OF THE PREFERRED EMBODIMENTS

Figure 1:
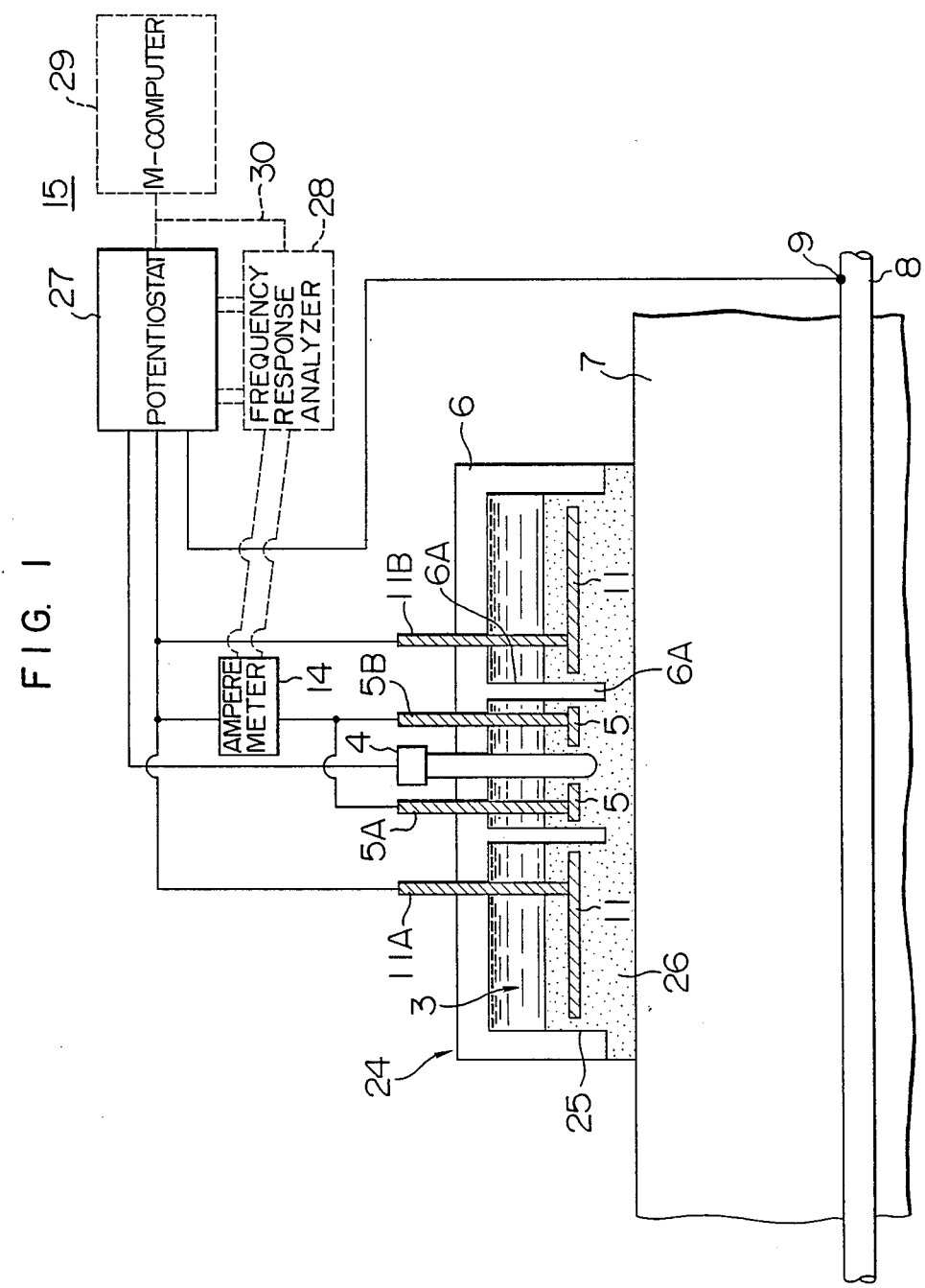
FIG. 1 is a view showing in section a structure of the corrosion detecting probe according to an embodiment of the present invention and an electrical wiring diagram for an electrochemical measuring apparatus used in combination with the inventive corrosion detecting probe.

Now, the present invention will be described in detail in conjunction with a preferred and exemplary embodiment thereof by first referring to FIG. 1, which shows a corrosion detecting probe 24 according to an embodiment of the invention and an electrochemical measuring apparatus 15 which are interconnected and mounted to inspect or examine the corrosion state (level) of a rod-like steel member 8 embedded in a concrete structure 7. The corrosion detecting probe 24 comprises a container 6 made of an insulation material and an electrode assembly mounted within the container 6. The container 6 is of a cylindrical configuration and has an open end 25 adapted to be placed in close or intimate contact with a surface of the concrete structure 7. The open end 25 is closed by a cover 26 made of a water permeable and electrically insulating porous material. The container 6 is interiorly filled with an electrolyte solution 3 so that the cover 26 of the water permeable material is sufficiently impregnated with the electrolyte solution 3. The electrode assembly includes a reference electrode 4, a counter electrode 5 and a current flow line control electrode 11, wherein at least portions of these electrodes located nearer to the concrete surface are embedded within the body of the cover 26.

The reference electrode 4 is implemented in a well known structure such that it includes a glass tube of an elongated cylindrical configuration having a small hole at its lower end portion and an electrode portion (not shown) mounted in the glass tube and having its end point extending through the small hole of the glass tube outside of the tube. The lower end portion of the reference electrode is inserted into the cover 6, while its upper end portion extends through the container 6 outwardly. Hereinafter, however, the electrode portion of the reference electrode is called as "reference electrode", in the specification and claims for simplicity of discription, unless otherwise noted to the effect. Bonded to the top end of reference electrode 4 is an electric wire for connection to the electrochemical measuring apparatus 15. The counter electrode 5 includes an annular electrode plate which encircles the free end portion of the reference electrode 4 at a distance therefrom and is connected to rod-like terminal member 5a and 5b which extend through the container 6 to the exterior. The annular electrode plate of the counter electrode lies substantially in parallel with the surface of the concrete structure 7 and hence with the longitudinal axis of the steel member 8 to be measured, when the corrosion detecting probe 24 is placed in close contact with the surface of the concrete structure 7. The current flow line control electrode 11 also includes an annular electrode plate disposed around the outer periphery of the electrode plate of the counter electrode 5 at a distance therefrom and is electrically connected to terminal members 11A and 11B extending through the container 6 to the exterior. The annular electrode plate of the current flow line control electrode 11 is in the same plane as that of the counter electrode 5 and is placed within the body of the electrolyte solution 3 or the cover 26 of water permeable material. The terminal bars 5A, 5B, 11A and 11B serve as connecting terminals for electrically connecting the respective electrodes to the electrochemical measuring apparatus 15 and at the same time serve to position the associated electrode plates positively by securing these terminal bars to the container 6. Although it is preferred that the gap between the electrode plates 5 and 11 be made as small as possible, both electrode plates must be positively prevented from contacting with each other. To this end, a partition wall 6A is provided to extend from the top wall of the container 6 downwardly through the space defined between the electrode plates 5 and 11, whereby the electrode plates 5 and 11 are positively protected against mutual contact. Preferably, the container 6 is made of an electrically insulating material such as synthetic resin while the counter electrode and the current flow line control electrode are made of an electrochemically stable material such as, for example, platinum. On the other hand, the cover 26 may be made of a porous material such as porous cork, laminated gauze or the like. The electrolyte solution may be a saturated solution of $Na_2SO_4$ or KCl. Finally, the terminal bars for the counter electrode and the current flow line control electrode should be made of a suitable electrically conductive material insusceptible to eroding action of the electrolyte.

In the case of the corrosion detecting probe of the structure described above, the electrode plates of the counter electrode and the current flow line control electrode are realized each in the form of annulus. However, the electrode plate is not necessarily restricted to such annular configuration, but each may be constituted by a pair of electrode plate segments disposed symmetrically with respect to the reference electrode 4. By way of example, the counter electrode and the current flow line control electrode can be constituted by pairs of electrode plate segments 5; 5' and 11; 11', respectively, disposed symmetrically to each other with respect to the reference electrode 4, as is shown in FIG. 1A. In this case, the electrode plates 5, 5', 11 and 11' are arrayed on and along a line. Upon use of the corrosion detecting probe, the latter is placed in close contact with the concrete surface in such orientation that the linear array of these electrode plates 5, 5', 11 and 11' extends in the longitudinal direction of the steel member to be measured.

As will now be understood from the foregoing description, the corrosion detecting probe according to the present invention differs from the one disclosed in JP-A-59-217147 in that the counter electrode 5 is disposed around the reference electrode 4 located at the center at a distance from the free end portion thereof and that the current flow line control electrode 11 is disposed around the counter electrode 5 at a distance therefrom such that the electrode plate of the former is flush with that of the latter or alternatively a pair of the current flow control electrode segments are disposed outside of a pair of the counter electrode segments at a predetermined distance from the former in a linear array and in a same plate. By virtue of the inventive structure of the corrosion detecting electrode assembly, the potential measurement can be accomplished with an improved accuracy with the reference electrode 4, and the quantitative electrochemical measurement can be realized because of the capability of detecting the current only from the limited area of the steel member located immediately underneath the counter electrode 5. Further, the corrosion detecting probe according to the present invention advantageously differs from those disclosed in Japanese Patent Publication No. 61-33380 in that the open end 25 of the corrosion detecting probe 24 is closed by the cover 26 of a water permeable material and that the container constituting the probe casing is interiorly filled with the electrolyte solution 3, wherein the reference electrode 4, the counter electrode 5 and the current flow line control electrode 11 are immersed in the electrolyte solution and preferably partially embedded in the water permeable cover 26.

This probe structure according to the invention allows improved electrical conduction to be assured between the probe and the steel member 8 embedded in the concrete structure. Additionally, due to the arrangement in which the reference electrode 4 is positioned at the center of the whole electrode array, the potential measurement is performed with high accuracy, whereby the quantitatively evaluable electrochemical measurement can be carried out.

It should be noted that the coplanar disposition of the counter electrode plate 5 and the current flow line control electrode plate 11 according to the teaching of the invention is for the purpose of preventing any appreciable potential difference from occurring between the counter electrode 5 and the current flow line control electrode 11. Further, such disposition in which the current control electrode plate 11 is positioned to enclose the counter electrode plate 5 at a distance from the outer periphery of the latter is based on the inventive concept that the area of the counter electrode 5 should be able to be utilized equivalently as the area of the steel material under inspection in evaluation of the measurement when the corrosion inspection is performed on a plate-like steel member buried in a concrete structure. Additionally, disposition of the paired current flow line control electrode segments 11 outside of the paired counter electrode segments 5 in a linear array with a distance from the latter, as is shown in FIG. 1A, is based on the contemplation that the area arithmetically determined from the electrode width of the counter electrode 5 as viewed in the longitudinal direction of the steel member under test and the circumferential length of the latter be evaluable as the area of the steel member under inspection when the object for measurement is such an elongated steel member as shown in FIG. 7.

The size of the counter electrode 5 of the corrosion detecting probe may be dimensioned appropriately for practical applications of the probe. In this conjunction, it should be mentioned that the accuracy of measurement can be more highly improved in principle when the current flow line control electrode 11 is increased in size as compared with that of the counter electrode 5. However, from the stand point of practical applications, the area of the current flow line control electrode 11 may be equal or greater than at least that of the counter electrode in the case of the corrosion detecting probe designed for the inspection of the steel material of a plate-like configuration. Same holds true in the case of measurement of reinforcing steel rod.

Figure 7:
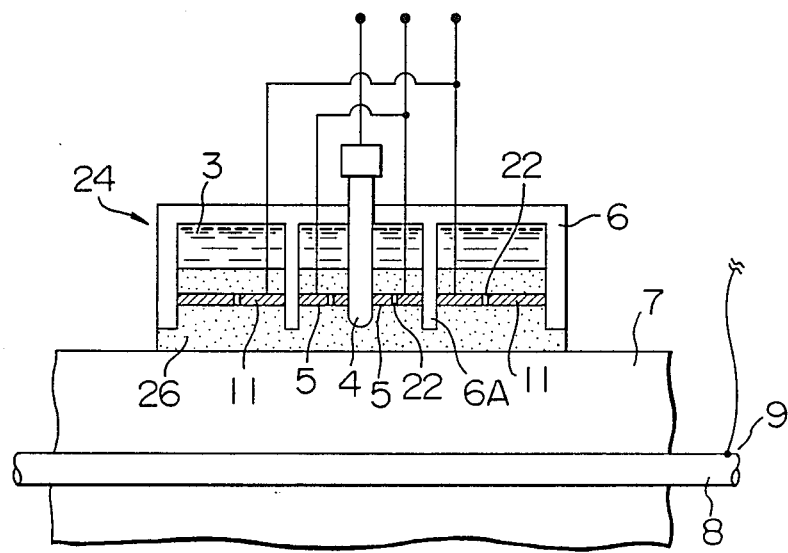
FIG. 7 is a view showing in section a structure of the corrosion detecting probe according to another embodiment of the present invention.
Figure 8:
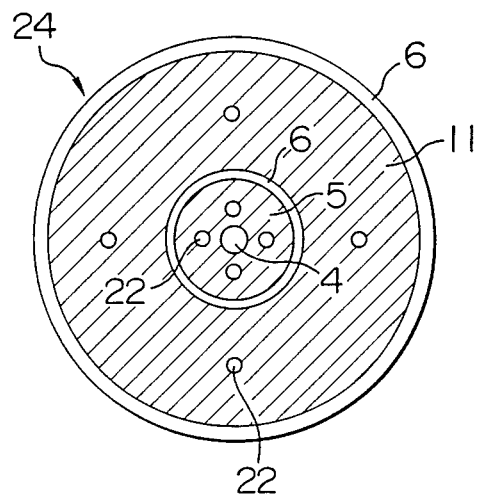
FIG. 8 is a sectional view taken along lines VIII—VIII of FIG. 7 showing a preferred electrode array for the corrosion detecting probe shown in FIG. 7.

With a view to insulating more positively the individual electrodes from one another and allowing only the end faces thereof facing the concrete surface to function as the effective electrode faces, there is proposed according to another embodiment of the present invention such a structure of the corrosion detecting probe as shown in FIGS. 7 and 8 in which the electrode plates 5 and 11 constituting the counter electrode and the current flow line control electrode, respectively, are fixedly secured in close contact with the inner wall of the container 6 and the inner partition wall 6A both of an electrically insulating material, wherein throughholes 22 are formed in the electrode plates 5 and 11 for allowing the electrolyte solution to flow outwardly. With this structure, the corrosion detecting probe provides higher accuracy in measurement.

The electrodes 5 and 11 as shown in FIG. 7 are made in the form of an annular plate, but each of these electrodes may be divided into a pair of electrode segments as shown in FIG. 1A which are disposed symmetrically with respect to the reference electrode. When the container 6, the counter electrode 5 and the current flow line electrode 11 are circularly configured and disposed coaxially around the reference electrode 4 located at the center, as is shown in FIG. 8, the corrosion detecting probe can be oriented at an arbitrary angle independent of the extending direction of the steel member under test. In other words, even when the object to be measured is an elongated steel member of straight length such as the reinforcing steel rod in an armored concrete structure, the corrosion detecting probe shown in FIGS. 7 and 8 can be oriented at any given angle to the elongated steel member, thus presenting improved convenience in use.

Further, the container 24 may be provided with a duct for the purpose of supplementing the electrolyte solution and for the purpose of degassing, as well as a tube equipped with a valve and a tank for supplementary electrolyte solution. However, since such equipment is known heretofore and constitutes no essential part of the invention, any further description thereof will be unnecessary.

Figure 1A:
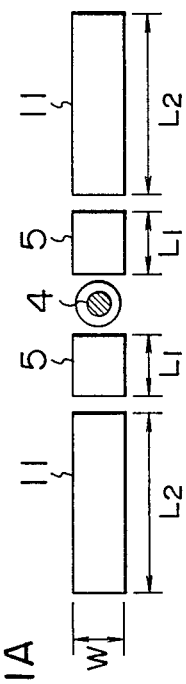
FIG. 1A is a schematic view showing a modified array of the individual electrodes constituting the corrosion detecting probe shown in FIG. 1.
Figure 2:
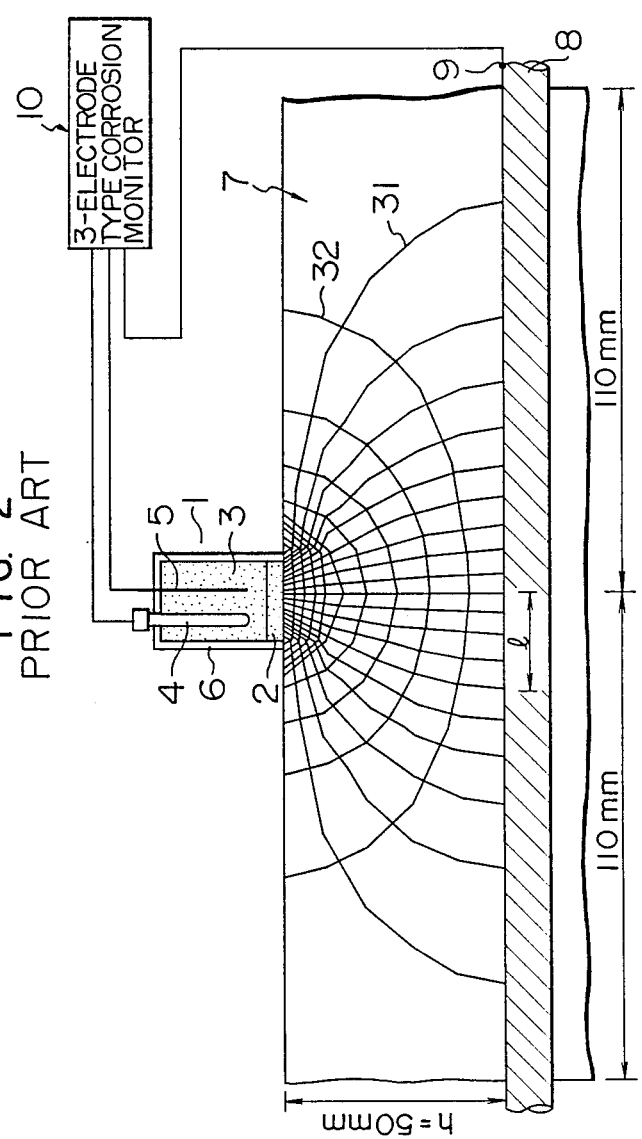
FIGS. 2 and 3 are views for illustrating the method disclosed in JP-A-59-21714.
Figure 3:
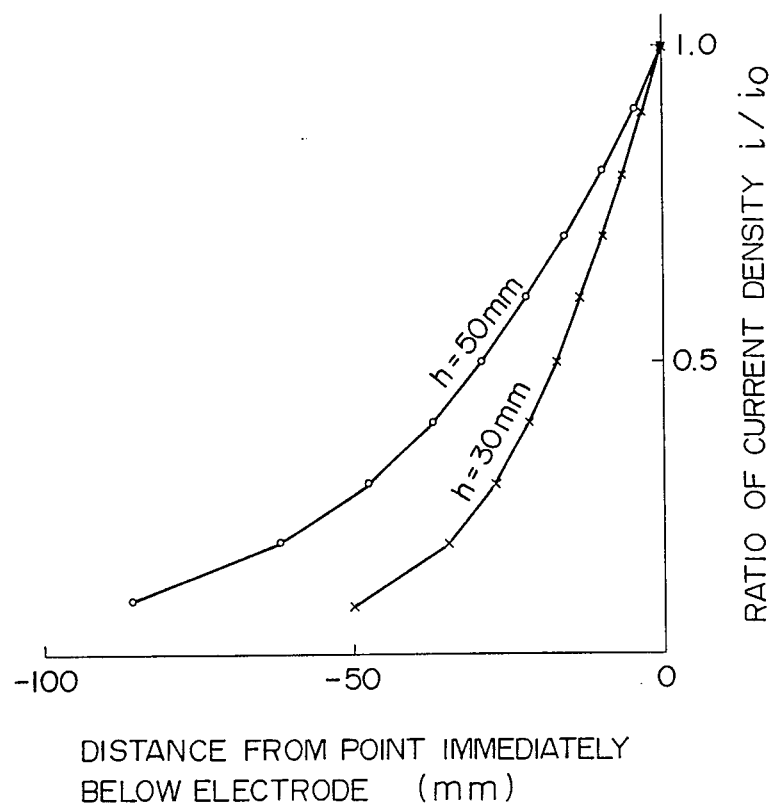
Figure 4:
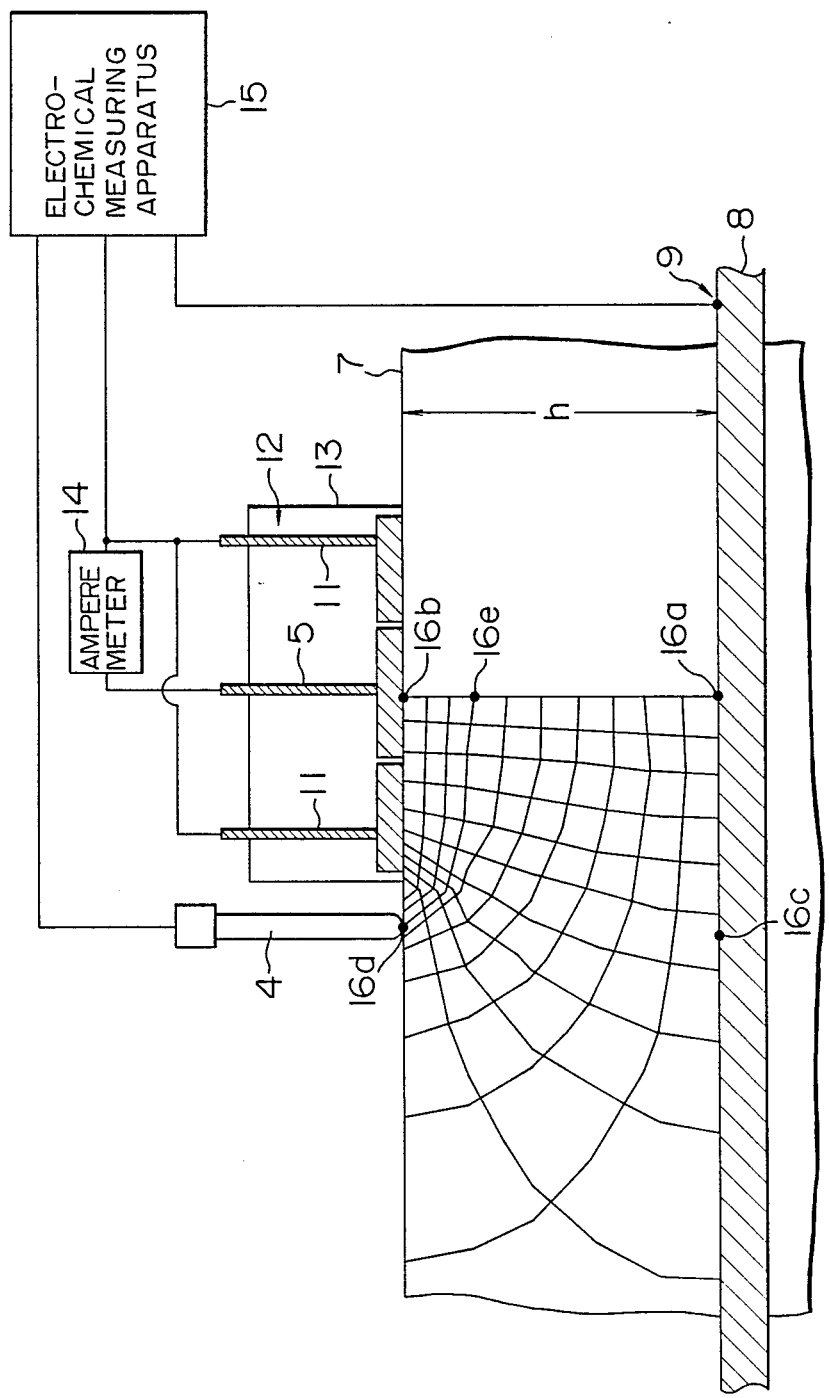
FIGS. 4, 5 and 6 are views for illustrating the method disclosed in Japanese Patent Publication No. 61-29457.
Figure 5:
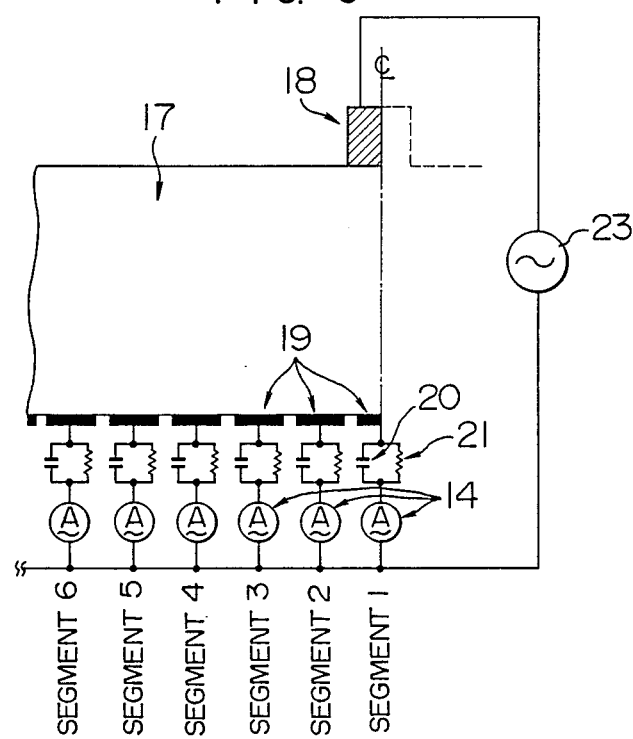
Figure 6:
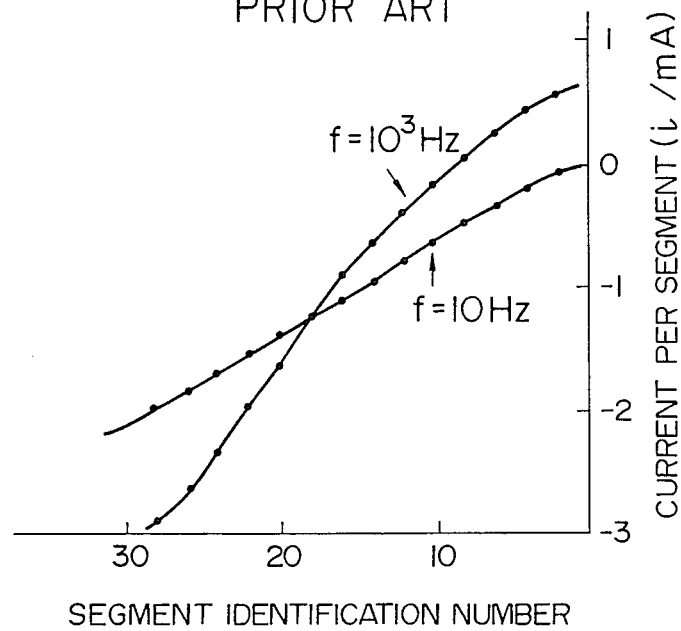
Figure 10:
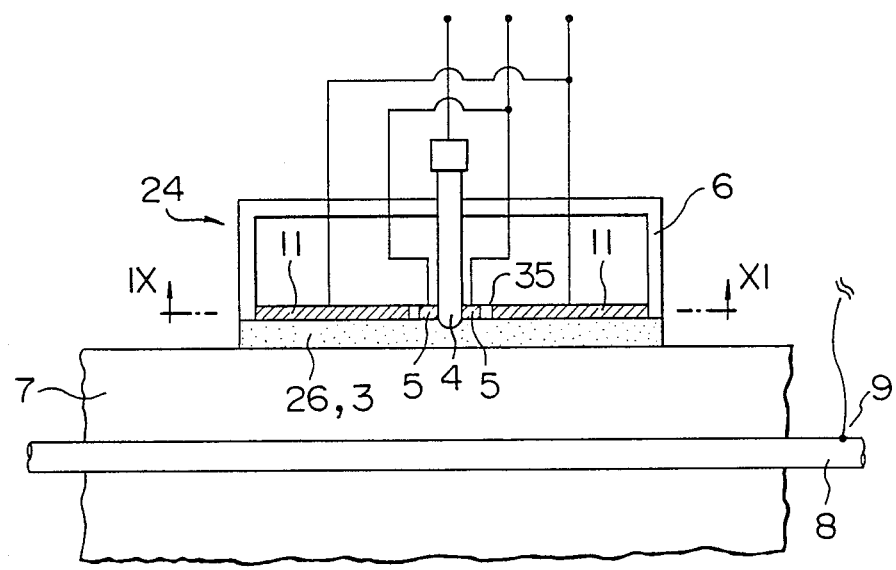
FIG. 10 is a schematic view showing in section a structure of the corrosion detecting probe according to still another embodiment of the present invention.
Figure 11:
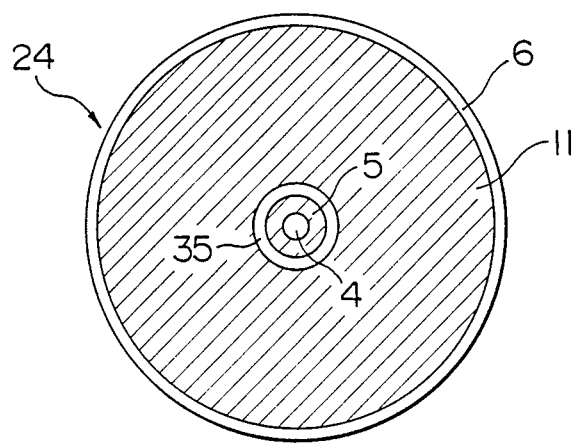
FIG. 11 is a sectional view along a line XI to XI' in FIG. 10.

Still another embodiment of the present invention is shown in FIGS. 10 and 11, in which the same components as those in FIG. 1 are designated by the same reference numerals. In the embodiment of FIGS. 10 and 11, the counter electrode 5 and the current line control electrode 11 are made concentrically with respect to the reference electrode 4 and fixed to each other by a spacer 35 made of an insulating material so that the electrodes 5 and 11 are formed integrally in a disk shape and the peripheral edge of the electrode 11 is fixed to the side wall of the container 6, while the internal edge of the electrode 5 is fixed by a suitable adhesive to the outer cover of the reference electrode 4. The cover 26 made of a water permeable and electrically insulating porous material is fitted into the open end of the container 6 with its upper surface in close contact with the lower surfaces of the electrodes 5 and 11. The lower end portion of the reference electrode 4 extends beyond the lower surface of the counter electrode 5. When the probe is not used, no electrolyte solution is filled in the container. Generally, the electrolyte solution 3 is filled into the container so as to have the cover 6 sufficiently impregnated with the electrolyte solution. Thus, it is possible to make the structure of the probe more simple.

Next, description will be turned to a method of electrochemical measuring the corrosion state of a steel material buried in a concrete structure with the corrosion detecting probe by again referring to FIG. 1.

As will be seen in FIG. 1, the corrosion detecting probe 24 is disposed on the surface of a concrete structure 7 such that the open end 25 of the container 6 is placed in close contact with the concrete surface at a position corresponding to a portion to be inspected. In this state, the various electrodes of the corrosion detecting probe and the steel member 8 are connected to an electrochemical measuring apparatus such as potentiostat known heretofore in the art for measuring electrochemically the rest potential, polarization resistance or AC impedance and the like. When it is desired to measure the corrosion state at a plurality of surface locations of the steel material, the corrosion detecting probe is sequentially moved to the corresponding points on the surface of the concrete 7 to perform the measurement in the manner mentioned above.

More specifically, the measurement of the rest potential can be easily and rapidly accomplished through combination of the corrosion detecting probe with a known electrometer. The rest potential as measured can be used for macro-evaluation of the state and nature of corrosion of the steel member buried in the concrete structure by referring to the criterion standards such as presented for example, in ASTM C876-77 "Half Cell Potentials of Reinforcing Steel" and others.

Further, measurement of polarization can be accomplished by measuring the current flowing to the counter electrode 5 by means of a non-resistance type ampere meter 14 by applying an appropriate potential between the counter electrode 5, which is electrically connected to the current flow line control electrode 11, and the steel member 8 from the potentiostat 27, the applied potential being determined in consideration of the rest potential determined in the manner described above. On the basis of a polarization curve thus obtained, a corrosion current $i_{corr}$ (A/cm$^2$) and hence the corrosion rate as well as presence or absence of passivated film can be determined. In this polarization measurement, compensation for ohmic drop in the concrete is naturally required, as with the case of the prior art measurement. However, since the ohmic drop of concern can be specifically determined as a function of only the thickness of the concrete coating, the compensation can be accomplished in a well known manner on the basis of the thickness of the concrete coating as well as electric resistance thereof measured by another measuring instrument also known heretofore.

Additionally, by using a frequency response analyzer 28 combined, if necessary, with a microcomputer 29 in addition to the arrangement shown in FIG. 1, measurement of AC impedance can also be carried out, impedance data thus obtained may be classified according to the method disclosed in "Collection of Preliminary Drafts for Lectures" p.p. 151-154, 1986 B-108 for the assembly held by Japanese Corrosion Protection Engineering Association for determining the presence or absence of the passivated film, the state of growth of rust, corrosion reacting resistance or corrosion rate and other.

EXAMPLE

A concrete specimen having a size of 400 mm×100 mm and incorporating a reinforcing steel rod of 19 mm in diameter buried at a depth h=15 mm was measured in respect to the AC impedance by using a corrosion detecting probe of the electrode array shown in FIG. 1A, in which the end point of the reference electrode is 2 mm in diameter, the counter electrode and the current flow line control electrode have respective lengths $L_1 = 5$ mm and $L_2 = 400$ mm and the same width $W = 10$ mm and the interelectrode gap is 1 mm. The container is made of a transparent acryl resin so that the state of electrolyte solution within the container can be externally observed. The liquid permeable material constituting the cover is made of gauze. A silver-silver chloride electrode is employed as the reference electrode with platinum wires and platinum meshes being used for the counter electrode and the current flow line control electrode. The electrolyte solution is a saturated $Na_2SO_4$-solution.

In the measurement of AC impedance, a voltage of sinusoidal waveform having an amplitude in a range of ±15 mV relative to the rest potential on the concrete surface is applied between the steel rod and the counter electrode connected to the current flow line control electrode, and response of the concrete specimen is measured in terms of current. The range of frequency is from 1 mHz to 10 KHz. In precedence to measurement, the concerned surface of the concrete specimen was wetted adequately with water tapped from a water service system.

The results of the measurement are graphically illustrated in FIG. 9. The plotted diagram is referred to as the Cole-Cole diagram, in which the imaginary component Zim (KΩ cm$^2$) of the measured impedance is taken along the ordinate with the real component Zre (KΩ cm$^2$) being taken along the abscissa. The values represented by a curve interconnecting a series of circles are obtained from the concrete specimen in which portions of the buried steel member not to be measured are covered with an insulating tape, while the curve attached with a series of marks x represents the result obtained from the unmasked portion of the steel bar. It will be seen that both curves well coincide with each other, which in turn shows that with the structure of the corrosion detecting probe according to the present invention, the quantitative electrochemical measurement can be realized for the steel material buried in the real concrete structure in the same manner as that in the conventional electrochemical measurement in which the test piece of steel member is coated with an insulating film at its outer surface other than its portion to be measured.

As will be seen from the foregoing description, the present invention makes it possible to conduct quantitative electrochemical measurement of a steel member buried in a concrete structure in the field for thereby allowing evaluation of the corrosion state of the steel material in a nondestructive manner.

We claim:

1. A corrosion detecting probe for inspecting the state of corrosion of a steel material buried in a concrete structure, comprising:

a container made of an electrically insulating material and including an open end adapted to be in close contact with a surface of a concrete layer coating of said steel material to be measured and closed by a cover member made of a water permeable porous material, said container being filled, at least when the probe is used, with an electrolyte solution to such a level that said cover is sufficiently impregnated with said electrolyte solution;

an electrode assembly immersed at least partially in said electrolyte solution and including a reference electrode, a counter electrode having an electrode plate of a configuration symmetrical with respect to said reference electrode and disposed outside of said reference electrode at a distance therefrom, and a current flow line control electrode having an electrode plate of a configuration symmetrical with respect to said reference electrode and disposed outside of said counter electrode at a distance from said counter electrode in a same plane as said electrode plate of said counter electrode; and terminal means for connecting said reference electrode, said counter electrode and said current flow line control electrode to an electrochemical measuring apparatus.

2. A corrosion detecting probe according to claim 1, wherein the electrode plate of said counter electrode is of an annular shape surrounding said reference electrode at a distance therefrom and the electrode plate of said current flow line control electrode is of an annular shape surrounding said annular electrode plate of said counter electrode at a distance therefrom.

3. A corrosion detecting probe according to claim 2, wherein said electrode plates of said counter electrode and said current flow line control electrode are disposed coaxially with respect to said reference electrode.

4. A corrosion detecting probe according to claim 1, wherein said counter electrode is composed of a pair of electrode segments disposed symmetrically with respect to said reference electrode at a distance therefrom, and said current flow line control electrode is composed of a pair of electrode segments disposed in alignment with said pair of the counter electrode segments and symmetrically with respect to said reference electrode.

5. A corrosion detecting probe according to claim 1, wherein said container includes a partition wall extending through a gap defined between the electrode plate of said counter electrode and that of said current flow line control electrode.

6. A corrosion detecting probe according to claim 1, wherein said reference electrode is fixedly centered in said electrode assembly.

* * * * *